United States Patent

Nabahi

[11] Patent Number: 6,103,256
[45] Date of Patent: Aug. 15, 2000

[54] INTRAVAGINAL DRUG DELIVERY DEVICE

[75] Inventor: Shohre Nabahi, Watchfield, United Kingdom

[73] Assignee: Hoechst Marion Roussel, France

[21] Appl. No.: 09/452,695

[22] Filed: Dec. 2, 1999

Related U.S. Application Data

[62] Division of application No. 09/102,302, Jun. 22, 1998, Pat. No. 6,039,968.

[30] Foreign Application Priority Data

Jun. 24, 1997 [GB] United Kingdom .................. 9713360
Nov. 24, 1997 [GB] United Kingdom .................. 9724777

[51] Int. Cl.[7] .............................. A61F 6/06; A61F 13/02; A61F 6/14

[52] U.S. Cl. .......................... 424/430; 424/431; 424/432; 424/433

[58] Field of Search ....................................... 424/430, 431, 424/432, 433

[56] References Cited

FOREIGN PATENT DOCUMENTS

887074A2  12/1998  European Pat. Off. .

Primary Examiner—Carlos A. Azpuru
Attorney, Agent, or Firm—Bierman, Muserlian and Lucas

[57] ABSTRACT

An intravaginal drug delivery device comprising at least one active agent dispersed in a polymer matrix, wherein the concentration of active agent at the outer surface of the device at the time of use is not substantially higher than the concentration of the active agent in the remainder of the device, a method of treatment therewith and a process for its preparation.

7 Claims, 6 Drawing Sheets

INTRAVAGINAL DRUG DELIVERY DEVICE

PRIOR APPLICATION

This application is a division of U.S. patent application Ser. No. 09/102,302 filed Jun. 22, 1998, now U.S. Pat. No. 6,039,968.

STATE OF THE ART

The present invention relates to intravaginal drug delivery devices. In particular, it relates to such devices suitable for the administration of a therapeutic agent, such as an oestrogen and/or a progestogen, at a substantially constant rate over a prolonged period of time, for example in the treatment of oestrogen deficiency or in a method of contraception.

17β-oestradiol ($E_2$) is the principal oestrogen produced by the functioning pre-menopausal ovary during each menstrual cycle. With the ageing process, ovulation becomes less frequent, resulting in diminished production of $E_2$. At the menopause, $E_2$ production decreases dramatically to less than 20 μg per day. Oestrogen deficiency can also occur in the pre-menopausal female as a result of disease, traumatic injury or oophorectomy.

Oestrogens, in particular 17β-oestradiol, are widely used for treating oestrogen deficiency, the aim being to replace endogenous oestrogens lost due to ovarian failure. Of the naturally occurring oestrogens, 17β-oestradiol ($E_2$) has the best therapeutic profile for Oestrogen Replacement Therapy (ERT) and Hormone Replacement Therapy (HRT) and has been found to have an especially low incidence of side effects. In particular, 17β-oestradiol does not stimulate clotting factor synthesis and is not associated with an increased risk of venous thrombosis. 17β-oestradiol and its semi-synthetic esters are therefore widely used in the treatment of disorders associated with oestrogen deficiency, in particular menopausal and post-menopausal symptoms.

Oestrogens and progestogens are also widely used in methods of contraception.

When taken orally, steroids in general are not particularly well absorbed, although after micronisation reasonable systemic levels can be achieved. Oral administration is followed primarily by absorption through the gastrointestinal tract from where the blood flow is to the liver. In general, oestrogens and progestogens have a high first pass and about 50 to 70% is metabolised during the first pass through the liver. As a result, oral therapy results in low bioavailability. Moreover, oral oestrogen therapy results in the formation of oestrone, a less potent oestrogen, which influences the blood lipid profile. This also means that there is about a 30% reduction in availability of oestrogen due to the first pass effect.

A further disadvantage associated with the oral administration of steroids is that it involves bolus doses resulting in undesirably high plasma levels after each dose and the need for frequent dosing.

An alternative to oral administration is subcutaneous implantation of oestrogen or progestogen-containing pellets, rods or oils. However, this requires medical supervision. For the delivery of oestrogen, transdermal drug delivery systems have also been proposed. However, these are not capable of producing the levels of oestrogen required for long term therapy and must be replaced every few days. Subcutaneous implants require surgical insertion and removal and are difficult to remove if dangerous side effects develop. Moreover, neither of these methods is capable of producing the constant levels of oestrogen or progestogen necessary for the treatment of oestrogen deficiency or for contraceptive use over a long period of time.

Vaginal administration of steroids overcomes a number of the problems associated with oral delivery. It is well known that steroids in general, including oestrogens and progestogens, are efficiently and rapidly absorbed through the vaginal mucosa. Moreover, delivery of oestrogen into the vagina is analogous to the secretion of oestrogen into the blood stream by the ovary and avoids undesirable first pass metabolism by the liver.

Oestrogen may be administered intravaginally using creams, solutions or tablets. However, as with oral administration, these result in bolus delivery rather than sustained levels of oestrogen and require repeated application. In order to achieve controlled, sustained release of oestrogen over a period of months, an intravaginal device, conveniently in the shape of a ring, has proved to be most effective. A particular advantage associated with the use of vaginal rings is that these can be self-inserted into and removed from the vagina.

There are three main types of ring design. The first is the matrix ring in which the active ingredient is distributed throughout a hydrophobic elastomeric system. The rate of release of active from a ring of this particular design is expressed by the equation given below (Chien 1985):

$$Q/t^{\frac{1}{2}} = (2ACp \cdot Dp)^{\frac{1}{2}}$$

where:
Q=amount of active released per unit area
A=concentration of the active in the matrix
Cp=solubility of active in the matrix
Dp=diffusion coefficient of the active in the matrix
t=time The second type of ring design is the core design in which the active ingredient is dispersed in a polymer matrix core surrounded by a rate-controlling sheath. The rate of drug release from a ring of this type can be expressed by the following equation (Crank 1967):

$$R = \frac{2\pi Cs \cdot D \cdot L}{\ln(b/a)}$$

where:
R=release rate
Cs=saturation solubility of active in the polymer matrix
D=diffusion coefficient of active in the polymer matrix
b=diameter of the sheath
a=diameter of the core
L=length of the core The third type of ring is the shell design in which the drug is contained in a narrow band between a non-medicated central hydrophobic elastomeric core and an outer sheath. The outer sheath acts as a rate-controlling membrane.

When using intravaginal devices for the delivery of therapeutic agents, it is desirable that the agent is released at a substantially constant rate over a prolonged period of time, preferably in the absence of high levels of release of the agent, particularly preferably in the absence of any initial high burst of agent during the first 24 hours following vaginal administration. This is particularly so when using such a device for the treatment of oestrogen deficiency or in a method of contraception.

In the case of rings of the matrix design, high initial loading with an active agent is possible, resulting in an initial high dose of active followed by a gradual decrease in the release rate. The rate of release of active agent over the first 2 or 3 weeks is also unacceptably high. Whilst intravaginal rings having a core or shell design are capable of a near zero order release of active, these too are characterised by an unacceptably high initial burst of active during the first 24 hours and/or over the first 15 or 21 days followed by a gradual decline to the desired release level. This high level of release of active in the first 24 hours and thereafter during the first 15 to 21 days can be associated with side effects which, depending on the nature of the active, may be serious. Thus, for example in the case of administration of 17β-oestradiol, an initial dose in excess of 700 μg over a period of 24 hours can cause increased risk of venous thrombosis.

OBJECTS OF THE INVENTION

There thus exists a need for intravaginal drug delivery devices capable of releasing an active or actives, such as oestrogen, in a substantially zero order pattern on a daily basis over a period of several months in the absence of any initial high rate of release of active.

BRIEF SUMMARY OF THE INVENTION

It has now surprisingly been found that wrapping an intravaginal drug delivery device with a removable polymer membrane is able to substantially reduce not only the initial high burst of active from the device following administration, e.g. during the first 24 hours of use, but also the levels of release of active during the first 3 weeks of use.

Thus, viewed from one aspect the invention provides an intravaginal drug delivery system having a first part intended for intravaginal administration ("an intravaginal part") comprising at least one active agent, such as an oestrogen and/or a progestogen, in a polymer matrix, said first part being provided in association with a second part comprising a removable polymer membrane arranged to absorb excess active agent.

By "removable" it is intended that the polymer membrane is arranged such that this can readily be removed from the intravaginal part by the patient or the physician prior to use or, alternatively, as an intermediate step during the manufacturing process. Conveniently, removal of the membrane may be achieved by simply tearing away the polymer membrane, for example along pre-formed tear lines or perforations provided in the membrane.

The polymer membrane may surround the intravaginal part either wholly or substantially. Preferably, the membrane wholly surrounds the intravaginal part.

Whilst not wishing to be bound by theoretical considerations it is believed that the initial high level of active released from vaginal rings of the core or shell design is a result of diffusion of the active from the surface of the core into the surrounding sheath during storage. This in turn results in an artificially high concentration gradient of active across the sheath and very close to the outer surface of the ring. Such an accumulation of active close to the surface of the ring is in excess of that which can be modelled using a matrix type distribution.

Similarly, it is believed that the high initial burst of active from rings of the matrix design is a result of a high level of active present on the surface of the ring. In these rings, the active is thus also believed to be present in much greater amounts at the outer surface of the ring.

Again not wishing to be bound by theory, it is believed that the polymer membrane serves to remove excess quantities of active from the surface of the intravaginal part of the system. This enables delivery of sustained, therapeutic quantities of active agent over extended periods of time, such as required in the delivery of oestrogen in Estrogen Replacement Therapy (ERT) and Hormone Replacement Therapy (HRT) or in the delivery of estrogens and progestogens in contraception, without any initial high burst of active.

In serving to effectively remove the high concentration of active at the outer surface of the intravaginal part of the system, the invention is capable of providing an intravaginal delivery device in which the active or actives are more homogeneously dispersed therein. Preferably, the active agent is substantially homogeneously dispersed throughout the polymer matrix.

Thus, viewed from another aspect the invention provides an intravaginal drug delivery device comprising at least one active agent, such as an oestrogen and/or a progestogen, dispersed in a polymer matrix, wherein the concentration of active agent at the outer surface of the device at the time of use is not substantially higher than the concentration of the active agent in the remainder of the device. Preferably, the active is substantially homogeneously dispersed throughout the device.

Yet more preferably, the concentration of active agent at the outer surface of the device is substantially lower than the concentration of the active agent in the remainder of the device. Thus, preferably the active is substantially homogeneously dispersed throughout the device, other than in close proximity to the surface.

Whilst it will be appreciated that the precise shape and dimensions of the polymer membrane will depend on the geometry of the device, the membrane should preferably be arranged such that this forms a relatively tight fit with the intravaginal part of the system. Thus, the polymer membrane should generally correspond to the shape of the intravaginal part. For example, in the case of a ring-shaped device the membrane will conveniently be toroidal in shape and its dimensions will be such that this lies in close contact with the outer surface of the intravaginal part.

The polymer membrane may be in direct contact with the intravaginal part. However, contact between the polymer membrane and the intravaginal part may be improved by smearing or coating the intravaginal part, either wholly or substantially, with an inert lubricant, e.g. a lubricating oil such as silicone, prior to wrapping with the polymer membrane. Examples of lubricants other than silicone which may be used to coat the intravaginal part prior to wrapping include other non-oxidising oils known to those skilled in the art. The use of a lubricant to coat the intravaginal part prior to wrapping also serves to aid ready removal of the polymer membrane by the patient or physician prior to use. Conveniently, any lubricant is removed from the intravaginal part, e.g. by washing, before use.

The polymer membrane may comprise any polymer material capable of absorbing an active from the intravaginal part and those skilled in the art will be aware of particular polymer materials suitable for this purpose. Whilst the particular choice of polymer for use as a membrane material will clearly depend on the active or actives to be delivered, polymers particularly suitable for use as a membrane material are those having a water vapour transmission (measured at a temperature of 20° C., a relative humidity of 85% and a film thickness of 50 μm) in the range of from 1 to 10,000 $g/m^2.d$, more preferably from 1 to 300 $g/m^2.d$, e.g. from 1 to 100 $g/m^2.d$ (wherein d=24 hours).

In general, any biocompatible polymer or mixture of such polymers may be used as the membrane material. Particularly suitable polymer materials include polyolefins such as polyethylene, polypropylene and polymethylpentene. Other polymers which may be used as the membrane material include polyvinylchloride, polyurethanes, polyamides and silicone elastomers such as organopolysiloxanes. Particularly preferred polymers are organopolysiloxanes, such as polydimethylsiloxanes and polyvinylmethylsiloxanes or mixtures thereof, optionally containing one or more fatty acid esters.

The thickness of the polymer membrane for use in accordance with the invention is dependent upon a number of factors, including the size, shape and specific design of the device, the amount and type of drug present in the device, and the period over which the device is intended to be stored in the membrane prior to use. Whilst those skilled in the art can readily determine the desired thickness for the polymer membrane for any given device, this will conveniently lie in the range of from 10 to 3000 $\mu$m, preferably from 10 to 2000 $\mu$m, more preferably from 30 to 1000 $\mu$m, e.g. from 30 to 100 $\mu$m.

As mentioned above, the thickness of the polymer membrane will be determined by the design of the ring, i.e. whether this is of the matrix, core or shell design. The membrane will be thickest for use with a matrix-type ring where a thickness of from 10 to 3000 $\mu$m is preferred. In the case of the core and shell designs, the use of a much thinner membrane is possible, e.g. one having a thickness of from 10 to 2000 $\mu$m.

The polymer matrix and polymer membrane may comprise one or more biocompatible polymers, for example elastomers such as organopolysiloxanes. Preferred elastomers include hydroxyl-terminated organopolysiloxanes of the RTV (room temperature vulcanizing) type which harden to elastomers at room temperature following the addition of cross-linking agents in the presence of curing catalysts. Suitable cross-linking agents and curing catalysts are known in the art. A typical curing catalyst is stannous octoate. Curing temperature and curing times can vary within broad ranges and depend on the particular elastomer used. The curing temperature may vary between room temperature and 150° C., but is preferably within the range of from 60 to 90° C. The curing time may vary between a few seconds to several hours.

Other suitable elastomers include two-component dimethylpolysiloxane compositions which are platinum catalysed at room temperature or under elevated temperatures and capable of addition cross-linking.

Preferred hydrophobic elastomers for use either as the polymer matrix or the polymer membrane material in the device according to the invention include Silastic 382® and Silastic 4210®, both commercially available from Dow Corning.

In a preferred embodiment of the invention, the intravaginal part of the device comprises a polymer matrix surrounded by a rate-controlling sheath through which the active can diffuse and which controls the rate of diffusion of active from the device into the vagina.

In a further embodiment of the invention, the intravaginal part comprises a core of inert elastomer, an active-containing polymer matrix encircling the core and an outer rate-controlling sheath through which the active can diffuse.

The sheath may comprise any bio-compatible polymer. Conveniently this will comprise the same polymer as the polymer matrix.

The polymer matrix and/or the rate-controlling sheath may further comprise one or more filler materials, such as diatomaceous earth or silica. In addition, the polymer matrix may comprise an X-ray contrast medium, such as barium sulphate, which can be used for identification purposes.

The polymer matrix, polymer membrane and/or the rate-controlling sheath may further comprise one or more rate modifying agents, such as a fatty acid ester, preferably one containing from 2 to 20 carbon atoms.

Preferred fatty acid esters for use in the device according to the invention include those formed from acids containing from 2 to 20 carbon atoms, especially long chain fatty acids, e.g. caproic, lauric, myristic, oleic, linoleic, adipic and lanolic acids. Particularly preferred are those esters formed from myristic acid. Alcohols which may be used in the formation of the esters include those containing from 2 to 20 carbon atoms, particularly those containing from 2 to 4 carbon atoms, e.g. propanol, in particular, isopropanol. A particularly preferred fatty acid ester is isopropyl myristate.

The amount of fatty acid ester present in the device will clearly depend upon the particular active to be delivered as well as the condition to be treated. Conveniently, the amount of fatty acid ester present in the device is from 1 to 50% by weight, preferably from 5 to 20% by weight. By suitable adjustment of the level of fatty acid ester present in the polymer matrix, a range of doses of active from rings of similar geometry can be achieved.

Whilst it should be apparent that the intravaginal device in accordance with the invention may have any shape and dimensions compatible with intravaginal administration, a preferred device according to the invention is in the form of a ring. This conveniently comprises a central annular polymer matrix core surrounded by an annular rate-controlling sheath.

Conveniently, the overall diameter of the ring is in the range of from 52 to 62 mm, with a sheath diameter (cross-sectional diameter of the ring) in the range of from 4 to 10 mm and a core diameter in the range of from 1 to 9 mm. The thickness of the rate-controlling sheath is such that it can be manufactured within acceptable tolerances by methods known in the art and conveniently lies within the range of from 1 to 4 mm, particularly from 1 to 3 mm. The geometry of the ring may be selected depending on the required daily dose of active and the duration of the course of treatment.

The intravaginal drug delivery device in accordance with the invention is considered to have utility in connection with the delivery of a wide range of therapeutic agents. As used herein, the terms "active" and "active agent" are used interchangeably and are intended to define any substance which in vivo is capable of producing a desired, usually beneficial, effect and may be an agent having either a therapeutic or a prophylactic effect.

Examples of active agents suitable for use in the device of the invention include agents in all of the major therapeutic areas including, but not limited to, anti-infectives such as antibiotics, antiviral and antifungal agents, analgesics, antidepressants, hormones and vitamins.

It will be appreciated that the desired amount of active agent present in the device will depend on the particular active being administered as well as the condition being treated. Convenient amounts of active, such as oestrogen, present in the device are from 1 to 50% by weight, preferably up to 15% by weight, more preferably from 5 to 15% by weight.

Conveniently, the device according to the invention can be used to effectively treat a number of conditions resulting from oestrogen deficiency, e.g. vasomotor symptoms associated with oestrogen deficiency, atrophic vaginitis, atrophic urethritis and osteoporosis associated with oestrogen deficiency. The device is particularly effective in hormone and oestrogen replacement therapies. Since fertility control involves the administration of sufficient oestrogen or progestogen to prevent ovulation, it will be appreciated that the delivery device-of the invention may also be used to prevent ovulation and thus act as an effective contraceptive. In this regard, the active may comprise one or more contraceptive steroids selected from ethinyl estradiol, levonorgestrel, d,l-norgestrel and norethindrone.

Oestrogens which can be delivered vaginally using the device according to the invention include oestrone and oestriol, in particular 17β-oestradiol which is widely used in hormone replacement therapy (HRT). Constant, daily release rates up to 500 μg per day for a period of up to 12 months can be achieved using a device in accordance with the invention. The desired rate of release of oestrogen depends on the condition to be treated but can be varied over a range of from 10 to 200 μg per day. A physiologically effective dose of 17β-oestradiol sufficient to treat postmenopausal symptoms is considered to be of the order of at least 50 μg per day. For use as a contraceptive device, 20 μg per day of levonorgestrel may be delivered.

Women who have undergone a hysterectomy with or without oophorectomy are at no risk from endometrial proliferation and can receive unopposed 17β-oestradiol. However, for women with an intact uterus, 17β-oestradiol therapy may conveniently be combined with a progestogen to reduce the risk of endometrial carcinoma.

Progestogens which can be delivered vaginally, either alone or in combination with an oestrogen, using the device according to the invention include any progestogens known to be suitable for use in hormonal replacement therapy and in contraception. Preferred progestogens include progesterone, medroxyprogesterone, norethisterone, norethisterone acetate and trimegestone. Convenient amounts of progestogen present in the device are from 1 to 50% by weight, preferably up to 15% by weight, more preferably from 5 to 15% by weight.

Other actives which can be administered using the device in accordance with the invention and their therapeutic use are listed by way of example only in the following table:

| ACTIVE | CATEGORY |
| --- | --- |
| Fluphenazine | Antidepressants/Anxiolytics |
| Flupenthixol | |
| Haloperidol | |
| Buspirone | P.M.S. Anxiolytics |
| Alprazolam | |
| Trifluoperzine | |
| Pyridoxine | P.M.S. Vitamin B6 |
| Pridoxal | |
| Pyridoxamine | |
| Cholecalciferol | Vitamin D |
| Dihydrotachysterol | |
| Ergocalciferol | |
| Alfacalcidol | |
| d-Alpha Tocopherol | Vitamin E |
| Clotrimazole | Antifungal |
| Enconazole | |
| Iltraconazole | |
| Buprenorphine | Opioid Analgesics |
| Levorphanol | |
| Phenoperidine | |
| Fentanyl | |

-continued

| ACTIVE | CATEGORY |
| --- | --- |
| Methadone | |
| Mefanamic Acid | Non-Opioid Analgesics |
| Acyclovir | Antiviral |
| Vidarabine | |
| Arildone | |
| Idoxuridine | |
| Gestrinone | Endometriosis |
| Mifepristone | |

Intravaginal drug delivery devices in accordance with the invention can be prepared by methods well known in the art, such as injection molding techniques or by melt extrusion of a polymer mixture. In this regard, the geometry of the device can be varied by the use of appropriately sized moulds or appropriately sized extrusion dies.

The method used to surround the device with the polymer membrane will depend on the geometry of the device. As mentioned previously, it is preferred that the polymer membrane lies in close contact with the device. This may be achieved in a number of ways, for example using injection moulding or extrusion techniques. Other techniques which may be used include coating of the device by a dipping process or winding an elongate strip of the polymer in the manner of a bandage around the device. Alternatively, a sheet of the polymer material may be wrapped around the device and secured in position e.g. using adhesive, welding or mechanical means such as stapling or stitching.

A preferred technique for wrapping the device comprises providing the device with a loose polymer sleeve and then removing the air using known vacuum sealing techniques such that the sleeve forms a tight seal around the device.

Viewed from a further aspect, the invention provides a method for the manufacture of an intravaginal drug delivery system in accordance with the invention, said method comprising the step of providing, preferably substantially surrounding, a polymer matrix containing at least one active agent with a removable polymer membrane arranged to absorb excess active agent.

Viewed from a yet further aspect, the invention provides a method for the manufacture of an intravaginal drug delivery system in accordance with the invention, said method comprising the following steps:

(a) dispersing at least one active agent, e.g. an oestrogen and/or a progestogen, in a polymer matrix whereby to form a core;

(b) optionally surrounding said core with a rate-controlling sheath; and (c) providing the resulting device with a removable polymer membrane capable of absorbing excess active agent.

Viewed from another aspect, the invention provides a process for preparing a ready-to-use intravaginal drug delivery device, said process comprising removal of a polymer wrapping from an intravaginal device or part as herein described.

The present invention will now be further described by way of the following non-limiting examples and with reference to the accompanying figures in which:

EXAMPLE 1

A silicone mix was prepared by mixing 97% by weight of polydimethylsiloxane (Silastic 3099® available from Dow Corning) with 2.5% by weight of the cross-linking agent n-propylorthosilicate (mix 1). 10% by weight of ethinyl estradiol (EE) was then added to a first portion of mix 1 and mixed thoroughly.

Appropriate quantities of the resulting mixture were then weighed and 0.5% by weight of the catalyst stannous octoate was added and mixed for one minute. The final mix was then injected into 2 mm core moulds and subsequently cured at 80° C. for two minutes. Ethinyl estradiol (EE) cores were then cut to length according to the dose required.

50% by weight of norethindrone acetate (NA) was added to a second portion of mix 1 and mixed thoroughly. Appropriate quantities of the resulting mixture were then weighed and 0.33% by weight of the catalyst stannous octoate was added and mixed for six minutes.

The final mix was then extruded using a 2 mm die and subsequently cured at 90° C. for one minute. Norethindrone acetate (NA) cores were then cut to length according to the dose required.

One NA and one EE core were then placed in a second mould. A sheath was formed around the cores by two-stage injection moulding of mix 1 together with 0.5% by weight of catalyst.

A number of the resulting rings were then smeared with a thin layer of silicone oil, wrapped in different polymers and left at ambient temperature for three weeks. After this time the polymer wrappings were removed, the rings washed and release tested by suspension in 200 ml of 0.133% benzalkonium chloride (BKC) solution. Release of NA and EE from these rings was compared with that from rings which had not been wrapped in any polymer material and which had been stored under similar conditions for a period of three weeks (control).

Figure 1:
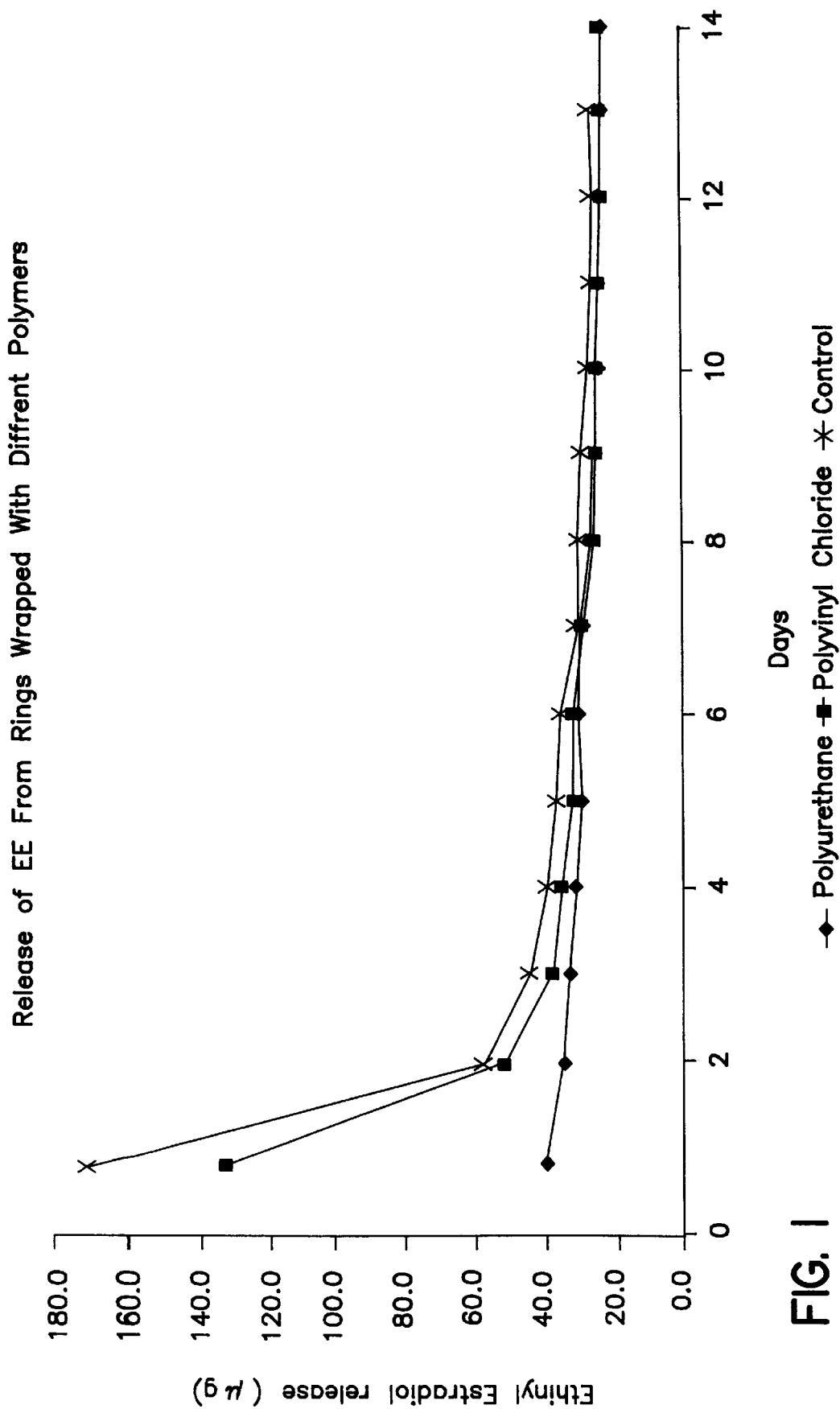
FIGS. 1 and 2 illustrate the release of ethinyl estradiol (EE) and norethindrone acetate (NA) from rings in accordance with the invention having a core diameter of 2 mm, a sheath diameter of 7.6 mm and a sheath thickness of 2.8 mm.
Figure 2:
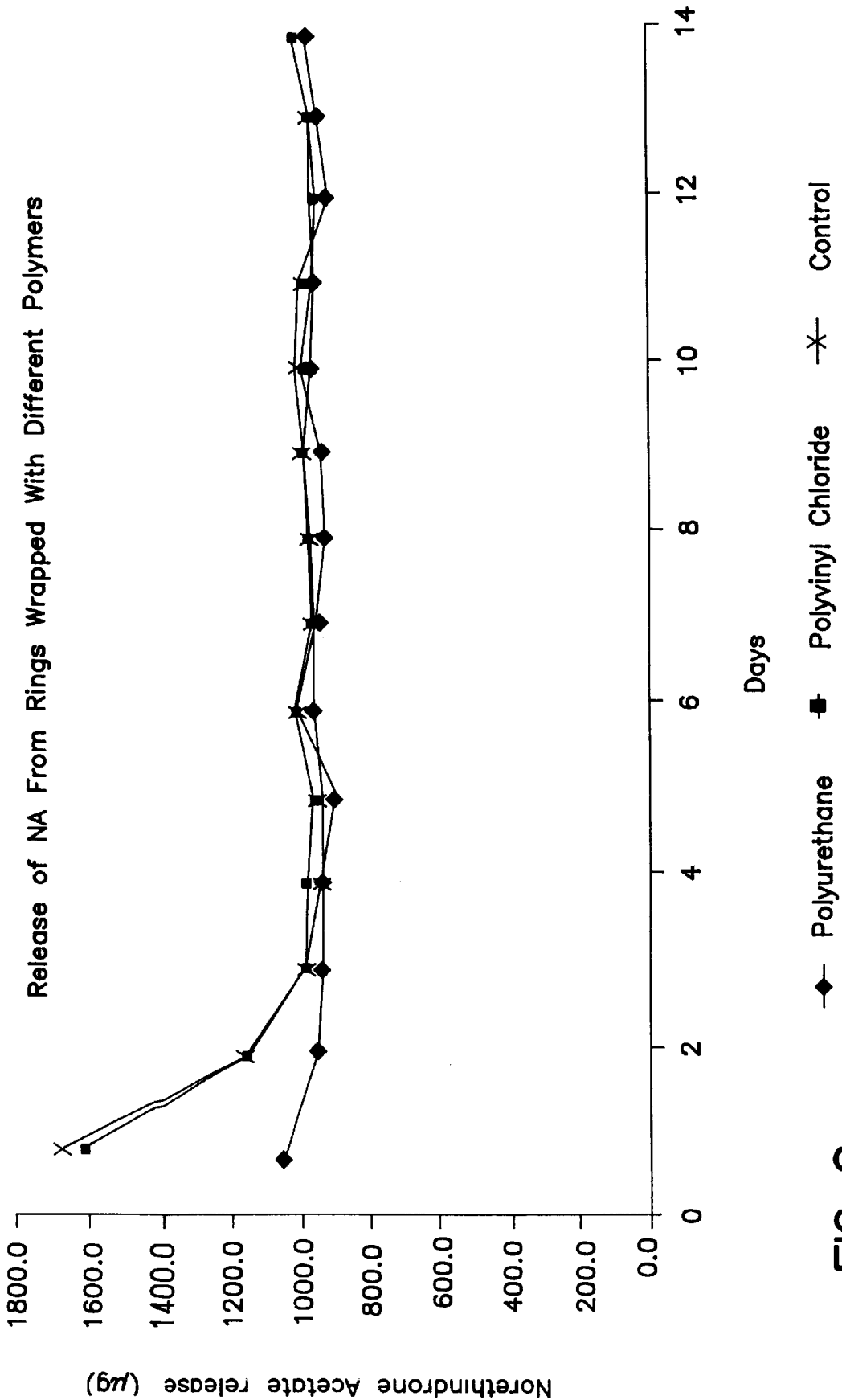

Tables 1 and 2 below and attached FIGS. 1 and 2 illustrate the rate of release of ethinyl estradiol (EE) and norethindrone acetate (NA) from these rings.

TABLE 1 first day release of EE from a ring designed to deliver 25 μg of EE before and after wrapping with polyurethane or polyvinyl chloride.

| | EE release (μg) | | |
|---|---|---|---|
| Time (hours) | Polyurethane | Polyvinyl chloride | Control |
| 0.25 | 0.0 | 13.2 | 20.8 |
| 0.5 | 0.0 | 19.3 | 29.6 |
| 1.0 | 0.0 | 27.5 | 41.6 |
| 2.0 | 0.0 | 39.9 | 59.9 |

TABLE 1-continued first day release of EE from a ring designed to deliver 25 μg of EE before and after wrapping with polyurethane or polyvinyl chloride.

| | EE release (μg) | | |
|---|---|---|---|
| Time (hours) | Polyurethane | Polyvinyl chloride | Control |
| 4.0 | 0.0 | 55.1 | 81.0 |
| 6.0 | 0.0 | 68.1 | 96.5 |
| 24.0 | 38.2 | 132.1 | 171.8 |

TABLE 2 first day release of NA from a ring designed to deliver 1000 μg of NA before and after wrapping with polyurethane or polyvinyl chloride.

| | NA release (μg) | | |
|---|---|---|---|
| Time (hours) | Polyurethane | Polyvinyl chloride | Control |
| 0.25 | 45.0 | 91.0 | 104.0 |
| 0.5 | 80.0 | 159.0 | 190.0 |
| 1.0 | 131.0 | 263.0 | 320.0 |
| 2.0 | 216.0 | 425.0 | 525.0 |
| 4.0 | 329.0 | 654.0 | 765.0 |
| 6.0 | 432.0 | 839.0 | 948.0 |
| 24.0 | 1031.0 | 1609.0 | 1669.0 |

EXAMPLE 2

A silicone mix was prepared by mixing 97% by weight of polydimethylsiloxane (Silastic 3099® available from Dow Corning) with 2.5% by weight of the cross-linking agent n-propylorthosilicate. The resulting mix was then blended in a ratio of 89% by weight with 11% by weight of isopropyl myristate (mix 1). 5% by weight of 17β-estradiol ($E_2$) was then added and mixed thoroughly.

Appropriate quantities of the above mix were then weighed and 0.5% by weight of the catalyst stannous octoate was added and mixed for one minute. The final mix was then injected into 4.5 mm core moulds and subsequently cured at 80° C. for two minutes.

The active cores were then removed from the moulds and placed in a second mould. A sheath was then formed around the core by two-stage injection moulding of mix 1 together with 0.5% by weight of catalyst.

A number of the resulting rings were then smeared with a thin layer of silicone oil, wrapped in different polymers and left at ambient temperature for three weeks. After this time the polymer wrappings were removed, the rings washed and subjected to in vitro release testing in one liter of water at 37° C. Release of $E_2$ from these rings was compared with that from rings which had not been wrapped in any polymer material and which had been stored under similar conditions for a period of three weeks (control).

Figure 3:
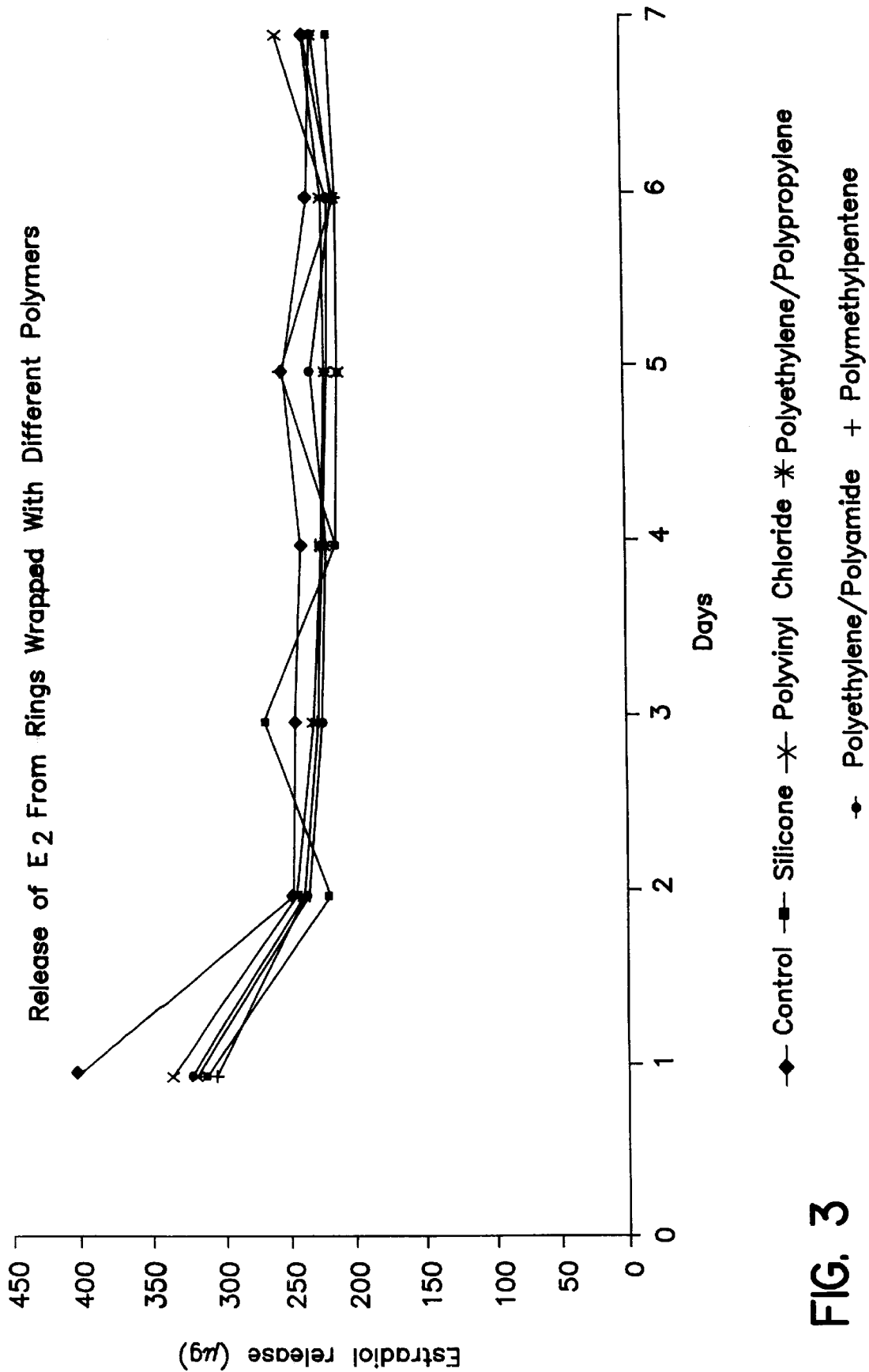
FIGS. 3 and 4 illustrate the release of 17β-estradiol ($E_2$) from rings in accordance with the invention having a core diameter of 4.5 mm, a sheath diameter of 7.6 mm and a sheath thickness of 1.55 mm.
Figure 4:
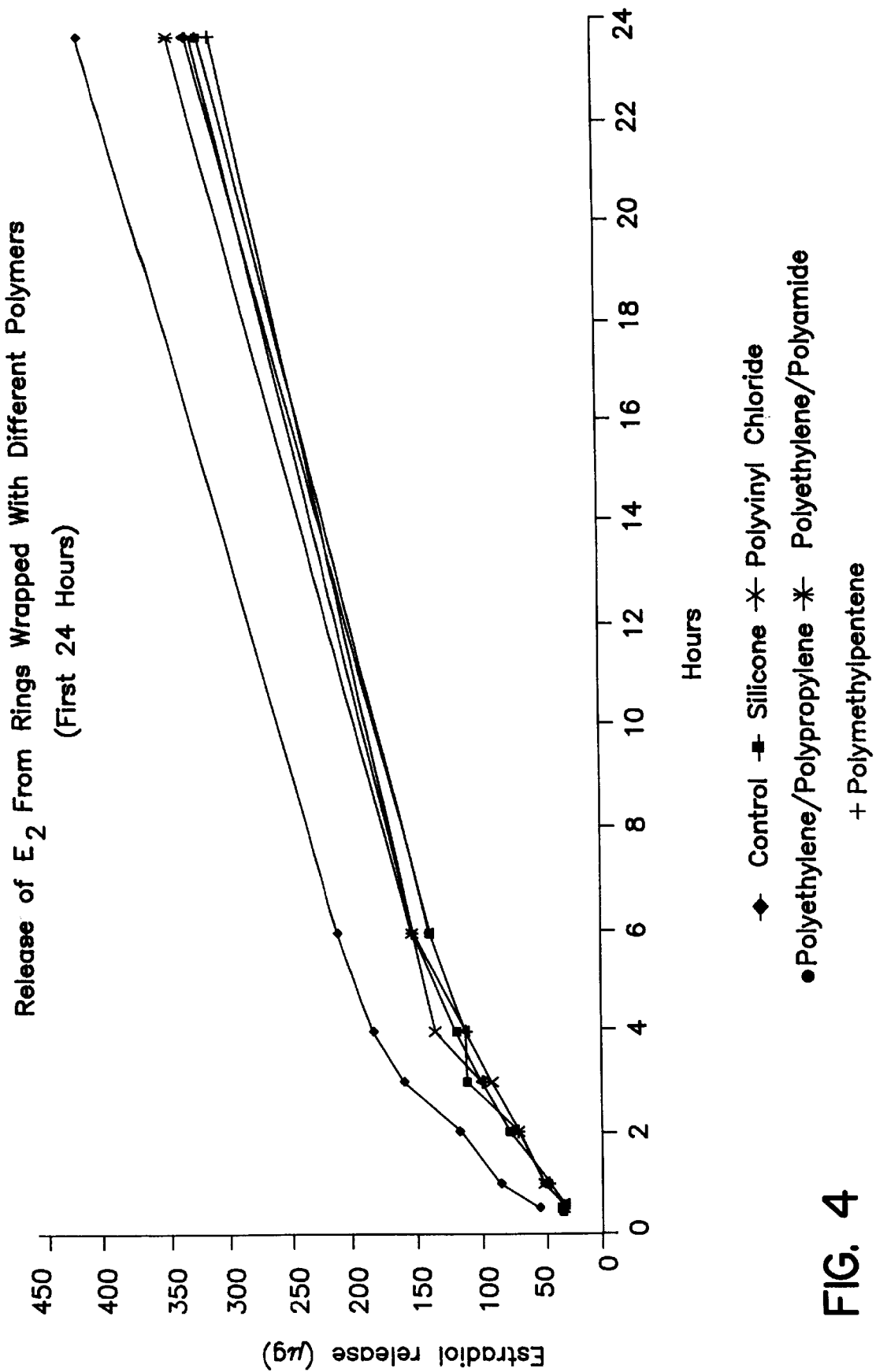

Table 3 below and attached FIGS. 3 and 4 illustrate the rate of release of $E_2$ from these rings.

TABLE 3 first day release of $E_2$ from a ring designed to deliver 200 μg of $E_2$ before and after wrapping with various polymer materials.

| | $E_2$ release (μg) | | | | | |
|---|---|---|---|---|---|---|
| Time | Control | Silicone | PVC | PE/PP | PE/PA | PMP |
| 0.5 | 55.3 | 31.8 | 31.2 | 33.6 | 32.2 | 30.2 |
| 1.0 | 85.3 | 47.2 | 47.8 | 49.6 | 48.6 | 44.4 |
| 2.0 | 114.7 | 69.6 | 68.5 | 74.8 | 75.2 | 67.9 |
| 3.0 | 154.9 | 106.9 | 88.9 | 94.8 | 97.3 | 89.9 |
| 4.0 | 178.2 | 110.3 | 109.7 | 131.6 | 115.9 | 106.2 |
| 6.0 | 209.1 | 136.2 | 136.5 | 150.4 | 148.4 | 149.6 |
| 24.0 | 408.0 | 314.0 | 322.3 | 339.4 | 326.4 | 306.9 |

PVC = polyvinyl chloride
PE = polyethylene
PP = polypropylene
PA = polyamide
PMP = polymethylpentene

EXAMPLE 3

Intravaginal rings were prepared in accordance with Example 1 using 3 mm cores. A number of the resulting rings were then vacuum wrapped in polyurethane and left at ambient temperature.

After periods of 1 week, 2 weeks and 3 weeks of wrapping, the polyurethane wrapping was removed and the rings were release tested in accordance with the procedure given in Example 1. Release of ethinyl estradiol (EE) from these rings was compared with that from rings which had not been wrapped in any polymer material and which had been stored under similar conditions (control).

Figure 5:
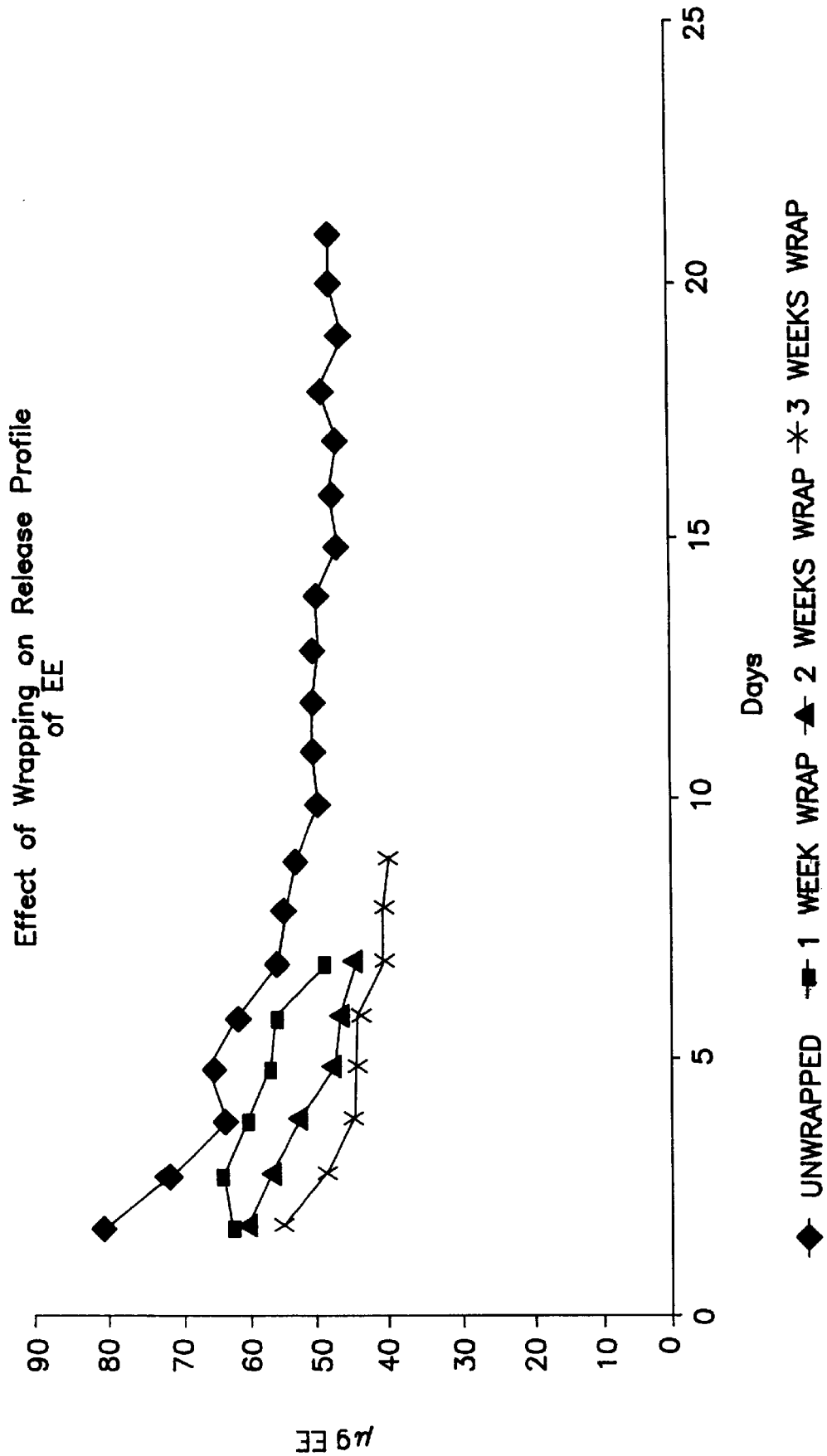
FIGS. 5 and 6 illustrate the release of ethinyl estradiol (EE) from rings in accordance with the invention having a core diameter of 3 mm, a sheath diameter of 7.6 mm and a sheath thickness of 2.3 mm.
Figure 6:
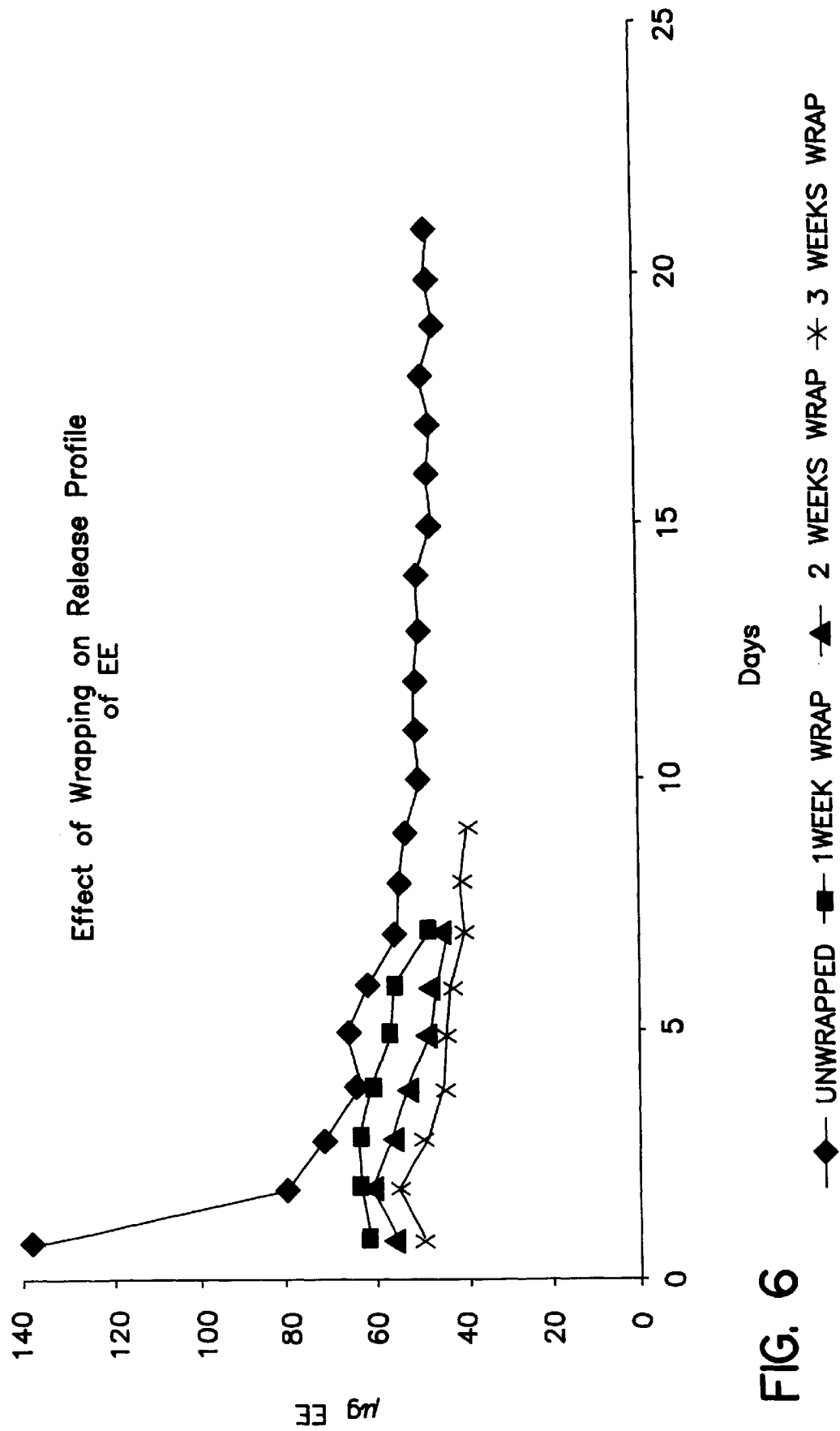

Attached FIGS. 5 and 6 illustrate the rate of release of EE from these rings. These clearly show that the first 10 days of release of EE is improved by the wrapping process.

What is claimed is:

1. An intravaginal drug delivery device comprising at least one active agent dispersed in a polymer matrix, wherein the concentration of active agent at the outer surface of the device at the time of use is not substantially higher than the concentration of the active agent in the remainder of the device.

2. A device as claimed in claim 1 wherein the concentration of active agent at the outer surface of the device is substantially lower than the concentration of the active agent in the remainder of the device.

3. A device as claimed in claim 1 wherein said active agent comprises an oestrogen and/or a progestogen.

4. A method of contraception of the human or non-human female body, said method comprising intravaginally administering to said body a device as claimed in claim 3.

5. A method of treatment of the human or non-human female body to combat conditions resulting from oestrogen deficiency, said method comprising intravaginally administering to said body a device as claimed in claim 3.

6. A process for preparing a ready-to-use intravaginal drug delivery device, said process comprising removal of a polymer wrapping from an intravaginal part, said intravaginal part comprising at least one active agent in a polymer matrix.

7. A process for preparing a ready-to-use intravaginal drug delivery device, said process comprising removal of a polymer wrapping from an intravaginal device, said intravaginal device comprising at least one active agent dispersed in a polymer matrix, wherein the concentration of active agent at the outer surface of the device at the time of use is not substantially higher than the concentration of the active agent in the remainder of the device.

* * * * *